US009804141B2

(12) United States Patent
Verbeck, IV et al.

(10) Patent No.: US 9,804,141 B2
(45) Date of Patent: Oct. 31, 2017

(54) METHOD FOR DETECTING ORGANIC AND INORGANIC EXPLOSIVES

(71) Applicant: 1ST DETECT CORPORATION, Austin, TX (US)

(72) Inventors: Guido Fridolin Verbeck, IV, Lewisville, TX (US); David Rafferty, Webster, TX (US); James Wylde, Oak Leaf, TX (US); Michael Spencer, Manvel, TX (US)

(73) Assignee: 1st Detect Corporation, Austin, TX (US)

( * ) Notice: Subject to any disclaimer, the term of this patent is extended or adjusted under 35 U.S.C. 154(b) by 79 days.

(21) Appl. No.: 14/280,175

(22) Filed: May 16, 2014

(65) Prior Publication Data

US 2015/0330961 A1 Nov. 19, 2015

(51) Int. Cl.
| | | |
|---|---|---|
| *G01N 33/22* | (2006.01) | |
| *G01N 1/44* | (2006.01) | |
| *G01N 1/28* | (2006.01) | |
| G01N 33/00 | (2006.01) | |
| G01N 1/40 | (2006.01) | |
| G01N 1/02 | (2006.01) | |
| G01N 1/38 | (2006.01) | |

(52) U.S. Cl.
CPC .......... *G01N 33/227* (2013.01); *G01N 1/28* (2013.01); *G01N 1/44* (2013.01); G01N 1/4022 (2013.01); G01N 1/4044 (2013.01); G01N 33/0057 (2013.01); G01N 2001/022 (2013.01); G01N 2001/383 (2013.01); Y10T 436/147777 (2015.01); Y10T 436/173076 (2015.01); Y10T 436/173845 (2015.01); Y10T 436/25375 (2015.01)

(58) Field of Classification Search
CPC ...... G01N 33/227; G01N 33/22; G01N 33/00; G01N 1/44; G01N 1/28; G01N 1/00; Y10T 436/14; Y10T 436/147777; Y10T 436/145555
USPC .............................................. 436/98, 96, 56
See application file for complete search history.

(56) References Cited

U.S. PATENT DOCUMENTS

| | | | | | |
|---|---|---|---|---|---|
| 5,480,612 | A | * | 1/1996 | Margalit | ................. G01N 31/22 422/430 |
| 6,121,008 | A | * | 9/2000 | Fitzpatrick | ........... G01N 33/558 422/562 |
| 7,846,740 | B2 | * | 12/2010 | Amisar | .................. G01N 31/22 422/423 |
| 8,377,713 | B2 | * | 2/2013 | Miller | ................ G01N 21/6428 422/430 |
| 2009/0029480 | A1 | * | 1/2009 | Loane | .................... G01N 21/78 436/170 |
| 2012/0149009 | A1 | * | 6/2012 | Levis | .................. H01J 49/0004 435/5 |

FOREIGN PATENT DOCUMENTS

WO  WO 2012177884 A1 * 12/2012  ........... G01N 1/4022

OTHER PUBLICATIONS

M. Sakayanagi et al., "Identification of Inorganic Anions by Gas Chromatography/Mass Spectrometry," Forensic Science International, 157 (2006), pp. 134-143.
Current Practice of Gas Chromatography—Mass Spectrometry, 2001, pp. 398-401.
H. Meng et al., "Simultaneous Determination of Inorganic Anions and Cations in Explosive Residues by Ion Chromatography," Talanta 76 (2008), pp. 241-245.
E. Tyrrell et al., "Coupled Reversed-Phase and Ion Chromatographic System for the Simultaneous Identification of Inorganic and Organic Explosives," J. Chromatogr. A, 1218 (2011), pp. 3007-3012.
Chromatography 6th Edition, Journal of Chromatography Library, vol. 69B (2004), pp. 530-531.

* cited by examiner

*Primary Examiner* — Christine T Mui
(74) *Attorney, Agent, or Firm* — Finnegan, Henderson, Farabow, Garrett & Dunner, LLP

(57) ABSTRACT

Methods, devices, and systems are disclosed for releasing a sample from a carrier medium. A method of releasing a sample from a carrier medium comprises treating a sample on a carrier medium with a first organic reagent, wherein when the sample contains at least one inorganic salt, the first organic reagent binds to a cation of the inorganic salt to produce both a first volatile compound and an isolated anion of the inorganic salt; treating the sample on the carrier medium with a second organic reagent, wherein the second organic reagent reacts with the isolated anion to produce a second volatile compound; and releasing the treated sample from the carrier medium, wherein when the first and the second volatile compounds are produced, the releasing step releases at least one of the first and second volatile compounds from the carrier medium.

40 Claims, 4 Drawing Sheets

```
┌─────────────────────────────┐
│  Spray sample with the first │
│       organic reagent        │
└─────────────────────────────┘
               │
               ▼
┌─────────────────────────────┐
│ Spray sample with the second │
│       organic reagent        │
└─────────────────────────────┘
               │
               ▼
┌─────────────────────────────┐
│ Release the treated sample from │
│       the carrier medium     │
└─────────────────────────────┘
```

FIG. 2

```
Evacuate sample chamber
          ↓
Spray sample with the first
     organic reagent
          ↓
Spray sample with the second
     organic reagent
          ↓
Release the treated sample from
     the carrier medium
```

FIG. 3

METHOD FOR DETECTING ORGANIC AND INORGANIC EXPLOSIVES

FIELD OF THE DISCLOSURE

The present disclosure relates to methods, devices, and systems for facilitating the release of a sample from a surface. More particularly, the present disclosure relates to methods, devices, and systems for releasing or desorbing a sample from a carrier medium by treating a sample with first and second organic reagents.

BACKGROUND OF THE DISCLOSURE

Chemical analysis tools such as gas chromatographs, mass spectrometers, ion mobility spectrometers, and various others, are commonly used to identify trace amounts of chemicals, including, for example, chemical warfare agents, explosives, narcotics, toxic industrial chemicals, volatile organic compounds, semi-volatile organic compounds, hydrocarbons, airborne contaminants, herbicides, pesticides, and various other hazardous contaminant emissions.

Most samples that undergo analysis for explosive material are heated to vaporize or release them from a carrier medium and are subsequently introduced into a chemical analyzer for detection. This technique is effective for detecting traditional organic explosives (e.g., TNT, NG, RDX). Inorganic salt-based explosives (e.g., permanganates, perchlorates, picrics, peroxides), however, have boiling points that are too high for practical vaporization by traditional thermal techniques. Thus, there is a need to develop new techniques that are capable of releasing both organic and inorganic explosive materials from a carrier medium. In addition, in order to be used in a wide range of applications, new techniques should be capable of quickly releasing organic and inorganic explosive materials from a carrier medium for subsequent analysis.

SUMMARY OF THE EMBODIMENTS

The present disclosure is directed to methods, devices, and systems for facilitating the release of a sample from a carrier medium. In a general aspect of the present disclosure, a method of releasing a sample from a carrier medium comprises treating a sample on a carrier medium with a first organic reagent; treating the sample on the carrier medium with a second organic reagent; and releasing the treated sample from the carrier medium.

In another general aspect, a method of releasing a sample from a carrier medium comprises treating a sample on a carrier medium with a first organic reagent, wherein when the sample contains at least one inorganic salt, the first organic reagent binds to a cation of the inorganic salt to produce both a first volatile compound and an isolated anion of the inorganic salt; treating the sample on the carrier medium with a second organic reagent, wherein the second organic reagent reacts with the isolated anion to produce a second volatile compound; and releasing the treated sample from the carrier medium, wherein when the first and the second volatile compounds are produced, the releasing step releases at least one of the first and second volatile compounds from the carrier medium.

In another general aspect, a method of releasing a sample from a carrier medium comprises treating a sample on a carrier medium, the sample comprising at least one inorganic salt, with a first organic reagent, wherein the first organic reagent binds to a cation of the inorganic salt to produce both a first volatile compound and an isolated anion of the inorganic salt; treating the sample on the carrier medium with a second organic reagent, wherein the second organic reagent reacts with the isolated anion of the inorganic salt to produce a second volatile compound; and releasing at least one of the first and the second volatile compounds from the carrier medium.

In some embodiments, the releasing step releases both the first and the second volatile compounds from the carrier medium. In some embodiments, the first and second volatile compounds are released from the carrier medium at the same time. In other embodiments, the first and second volatile compounds are released from the carrier medium at different times.

In some embodiments, the first organic reagent comprises a polar aprotic solvent. In certain embodiments, the first organic reagent is dimethyl sulfoxide (DMSO).

In some embodiments, the second organic reagent comprises an organic reagent capable of undergoing a nucleophilic substitution reaction with the isolated anion. In some embodiments, the second organic reagent comprises a leaving group. In certain embodiments, the leaving group is sulfonate. In certain embodiments, the second organic reagent is pentafluorobenzyl-toluenesulfonate (PFB-Tos).

In some embodiments, the first organic reagent is DMSO and the second organic reagent is a perfluoroaryl sulfonate. In certain embodiments, the perfluoroaryl sulfonate is PFB-Tos.

In some embodiments, treating a sample on a carrier medium with a first organic reagent and treating the sample on the carrier medium with a second organic reagent occurs at the same time or in a single step.

In some embodiments, releasing the treated sample from the carrier medium comprises at least one technique chosen from reducing pressure on the treated sample and heating the treated sample. As used herein, "reducing pressure on the treated sample" means reducing the pressure of the surrounding medium, such as reducing the internal pressure of a container (e.g., a sealed sample chamber) housing the treated sample.

The method may further comprise introducing the released sample into a chemical analyzer.

In some embodiments, the sample on a carrier medium is treated with the first and second organic reagents external to a sample chamber. The method may further comprise depositing the carrier medium carrying the treated sample into the sample chamber prior to releasing the treated sample. The sample chamber may be coupled to a chemical analyzer. In some of embodiments, the sample on the carrier medium is treated with the first and second organic reagents by spraying the first and second organic reagents on the carrier medium. In some embodiments, the treated sample on the carrier medium is transferred from another carrier medium, such as a pad, wipe, swab, or any other object that may be used to collect a sample. In certain embodiments, the second organic reagent is sprayed on a carrier medium after or at the same as spraying the first organic reagent on the carrier medium. In certain embodiments, a carrier medium is pre-impregnated with one or both of the first and second organic reagents such that when the carrier medium contacts a sample, the sample is treated with one or both of the first and second organic reagents. The treated sample may then be released from the carrier medium in a sample chamber.

In other embodiments of the present disclosure, the sample on a carrier medium is treated with the first and second organic reagents inside of a sample chamber. The sample chamber may be coupled to a chemical analyzer. In certain embodiments, the sample on a carrier medium inside of the sample chamber is treated with the first and second organic reagents by spraying the first and second organic reagents on the carrier medium. In some embodiments, the second organic reagent may be sprayed on the carrier medium after or at the same as spraying the first organic reagent on the carrier medium.

The sample chamber may be coupled to a vacuum pump capable of reducing the pressure within the sample chamber. In some embodiments, the vacuum pump may be directly coupled to the sample chamber. In some embodiments, the vacuum pump may be coupled to a chemical analyzer, such as directly coupled to the chemical analyzer, which is coupled to the sample chamber. The sample chamber may also be coupled to a roughing pump, such as directly coupled to a roughing pump.

In some embodiments, releasing the treated sample from the carrier medium comprises at least one technique chosen from reducing pressure on the treated sample and heating the treated sample. In some embodiments, releasing the treated sample from the carrier medium comprises reducing pressure on the treated sample and heating the treated sample. Reducing pressure on the treated sample and heating the treated sample may occur at the same time or at different times. For example, releasing the treated sample from the carrier medium may comprise heating the treated sample after reducing pressure on the treated sample. Reducing pressure on the treated sample may comprise evacuating a sample chamber housing the treated sample to reduce an internal pressure of the sample chamber to a level less than atmospheric pressure. In some embodiments, the sample chamber is evacuated using a vacuum pump directly coupled to the sample chamber. In some embodiments, the sample chamber is evacuated using a vacuum pump directly coupled to a chemical analyzer. In some embodiments, the released sample is introduced into a chemical analyzer during evacuation of the sample chamber. In some embodiments, the released sample is introduced into a chemical analyzer after evacuation of the sample chamber.

In some embodiments, the method further comprises evacuating a sample chamber housing the sample to reduce an internal pressure of the sample chamber to a level less than atmospheric pressure prior to treating the sample with the first and second organic reagents. In some embodiments, the sample chamber is evacuated using a vacuum or roughing pump. In certain embodiments, the sample chamber is evacuated to an internal pressure below atmospheric pressure but greater than the vapor pressures of the first and second volatile compounds. In other embodiments, the sample chamber is evacuated to an internal pressure below atmospheric pressure and equal to or less than the vapor pressures of one or both of the first and second volatile compounds, leading to the release of one or both of the first and second volatile compounds upon treating the sample with the first and second organic reagents. Thus, there is disclosed a method of releasing a sample from a carrier medium comprising evacuating a sample chamber housing a sample on a carrier medium to an internal pressure at least below atmospheric pressure and treating the sample on a carrier medium with a first organic reagent and a second organic reagent.

The method may further comprise introducing the released sample into a chemical analyzer. In some embodiments, the step of releasing the sample from the carrier medium includes introducing the released sample into a chemical analyzer.

In another general aspect of the present disclosure, a sample chamber for releasing a sample from a carrier medium comprises a base and a lid forming a cavity configured to receive a carrier medium carrying a sample, and a spraying system configured to spray one or more reagents on the carrier medium, wherein the sample chamber is configured to be coupled to a chemical analyzer.

In yet another general aspect of the present disclosure, a sample analysis system comprises a sample chamber configured to receive a carrier medium carrying a sample, wherein the sample chamber comprises a base and a lid operable to access a cavity formed by the base and the lid, a spraying system configured to spray one or more reagents on the carrier medium; and a chemical analyzer coupled to the sample chamber and configured to receive the sample from the sample chamber.

The preceding summary is not intended to restrict in any way the scope of the claimed invention. In addition, it is to be understood that both the foregoing general description and the following detailed description are exemplary and explanatory only and are not restrictive of the invention, as claimed.

The accompanying drawings, which are incorporated in and constitute a part of this specification, illustrate various embodiments and exemplary aspects of the present invention and, together with the description, explain principles of the invention.

BRIEF DESCRIPTION OF THE DRAWINGS

FIG. 2 illustrates a process flow diagram of an exemplary method for releasing a sample from a carrier medium.

FIG. 3 illustrates a process flow diagram of another exemplary method for releasing a sample from a carrier medium.

DETAILED DESCRIPTION OF THE EMBODIMENTS

Figure 1:
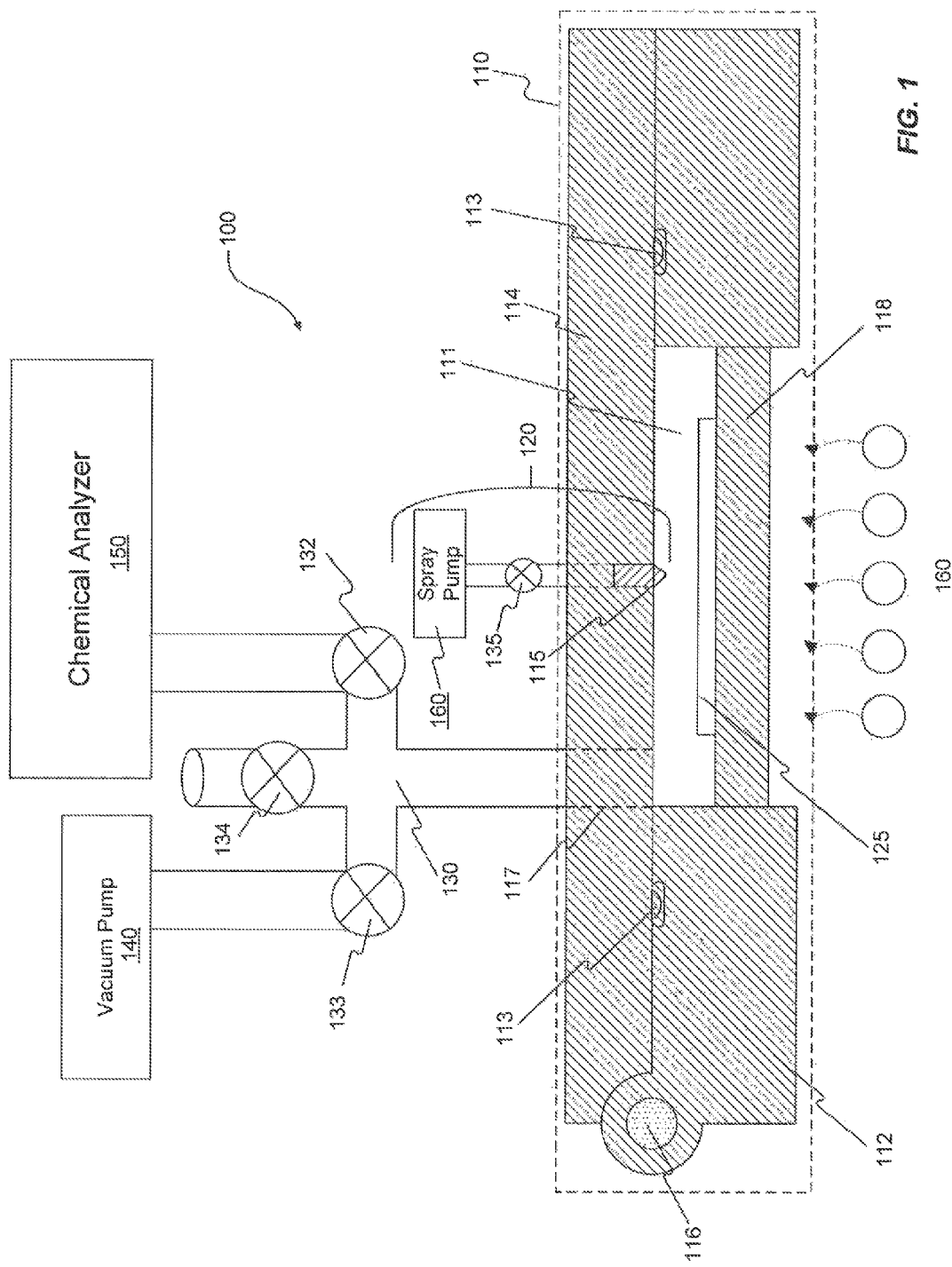
FIG. 1 is a schematic diagram of an exemplary chemical detection system, in accordance with some disclosed embodiments.

Reference will now be made in detail to exemplary embodiments of the invention, examples of which are illustrated in the accompanying drawings. When appropriate, the same reference numbers are used throughout the drawings to refer to the same or like parts.

The terms "release" and "desorb" are used interchangeably herein.

Embodiments of the present disclosure involve methods, apparatuses, and systems for releasing a sample from a carrier medium. Releasing or desorbing a sample from a carrier medium may permit the sample to be subjected to further processing. For example, a sample that has been released from a carrier medium by vaporization may be introduced into a chemical analyzer for analysis. The ability to release a sample from a carrier medium and subject it to chemical analysis is particularly important for the detection of explosive materials. The emergence of homemade and improvised explosives has expanded the number of compounds to be detected with trace explosives detectors.

The present disclosure provides techniques for releasing a sample from a carrier medium, wherein the techniques are capable of releasing inorganic salts, such as inorganic salt-based explosives (e.g., ammonium perchlorate), from the carrier medium by transforming the inorganic salts into volatile compounds. These volatile compounds can be released from a carrier medium such that the entire composition of an inorganic salt, i.e., the cation and the anion, can be determined using a chemical analyzer. The present techniques can also release organic compounds, such as organic explosives (e.g., TNT, NG, RDX), from a carrier medium. Thus, the techniques disclosed herein allow for both inorganic and organic explosive materials present in a sample to be released from a carrier medium for further processing.

Accordingly, there is disclosed a method of releasing a sample from a carrier medium comprises treating a sample on a carrier medium with a first organic reagent; treating the sample on the carrier medium with a second organic reagent; and releasing the treated sample from the carrier medium.

There is also disclosed, a method of releasing a sample from a carrier medium comprising treating a sample on a carrier medium with a first organic reagent, wherein when the sample contains at least one inorganic salt, the first organic reagent binds to a cation of the inorganic salt to produce both a first volatile compound and an isolated anion of the inorganic salt; treating the sample on the carrier medium with a second organic reagent, wherein the second organic reagent reacts with the isolated anion to produce a second volatile compound; and releasing the treated sample from the carrier medium, wherein when the first and the second volatile compounds are produced, the releasing step releases at least one of the first and second volatile compounds from the carrier medium.

There is also disclosed, a method of releasing a sample from a carrier medium comprising treating a sample on a carrier medium, the sample comprising at least one inorganic salt, with a first organic reagent, wherein the first organic reagent binds to a cation of the inorganic salt to produce both a first volatile compound and an isolated anion of the inorganic salt; treating the sample on the carrier medium with a second organic reagent, wherein the second organic reagent reacts with the isolated anion of the inorganic salt to produce a second volatile compound; and releasing at least one of the first and the second volatile compounds from the carrier medium.

When a sample is referred to herein as being "on" a carrier medium, the sample may be on the carrier medium, such as being located in a pore and/or crevice of the carrier medium, in the carrier medium (e.g., taken up by a sorbent carrier medium), or oriented with respect to the carrier medium in any manner such that the carrier medium is carrying the sample. As used herein, a carrier medium may be any object or material capable of carrying a sample. For example, the carrier medium may be clothing, shoes, papers, handbags, luggage, handheld devices, soil, etc. In some embodiments, the carrier medium is a pad, wipe, swab, or any other object that may be used to collect a sample by, for example, wiping the surface of a target object or being dipped into a target substance. In some embodiments, the carrier medium comprises one or more sorbent materials, such as carbon cloth material, polytetrafluoroethylene (PTFE), polystyrene, cotton, or SPME metal alloy fiber assembly having a polydimethylsiloxane (PDMS) or other coating.

According to the methods of the present disclosure, the first organic reagent is capable of binding to a cation of an inorganic salt to produce both a first volatile compound and an isolated anion of the inorganic salt. Subsequent release of the first volatile compound from the carrier medium allows for the first volatile compound to be introduced into a chemical analyzer. The chemical analyzer can be used to detect the presence of the first volatile compound, resulting in the identification of the cation of the inorganic salt.

The second organic reagent is capable of reacting with the isolated anion of the inorganic salt to produce a second volatile compound. Subsequent release of the second volatile compound from the carrier medium allows for the second volatile compound to be introduced into a chemical analyzer. The chemical analyzer can be used to detect the presence of the second volatile compound, resulting in the identification of the anion of the inorganic salt.

As described herein, the first and second volatile compounds may be released and introduced into the chemical analyzer simultaneously or at different times.

Shown below is a generalized example of a chemical process that occurs when a sample containing an inorganic salt is treated with the first and second organic reagents.

$$AB + X_1 \rightarrow Y_1A + B$$

$$B + X_2 \rightarrow Y_2B$$

AB=Inorganic Salt   $Y_1A$=First Volatile Compound
A=Cation   B=Anion (Isolated)
B=Anion   $Y_2B$=Second Volatile Compound
$X_1$=First Organic Reagent
$X_2$=Second Organic Reagent The first organic reagent may comprise a polar aprotic solvent. "Polar aprotic solvent" as used herein means a polar aprotic solvent having a dielectric constant of at least 37. In some embodiments, the polar aprotic solvent is chosen from dimethyl sulfoxide (DMSO), dimethylformamide (DMF), dimethylacetamide (DMAC), propylene carbonate, and sulfolane. In certain embodiments, the first organic reagent is DMSO.

The second organic reagent may comprise an organic reagent capable of undergoing nucleophilic substitution with the isolated anion. In certain embodiments, the organic reagent capable of undergoing nucleophilic substitution with the isolated anion comprises a sulfonate leaving group, such as optionally substituted alkyl or aryl sulfonate. In some embodiments, the second organic reagent comprises a compound having at least one electron-withdrawing group. In certain embodiments, the second organic reagent comprises at least one of an optionally substituted alkyl halide and optionally substituted aryl halide. In certain embodiments, the second organic reagent comprises a hydrofluorocarbon, a fluorocarbon, or a derivative thereof, such as a perfluorinated compound. In some embodiments, the hydrofluorocarbon has a majority of points of saturation with a fluorine atom. Examples of perfluorinated compounds include perfluoroalkyl and perfluoroaryl compounds. In certain embodiments, the second organic reagent is a perfluoroalkyl sulfonate or a perfluoroaryl sulfonate. In certain embodiments the perfluoroaryl sulfonate is pentafluorobenzyl-toluenesulfonate (PFB-Tos).

In a specific, non-limiting embodiment of the present disclosure, the first organic reagent is DMSO and the second organic reagent is PFB-Tos. In the context of this particularized embodiment, shown below is a reaction scheme that occurs when a sample contains the inorganic salt-based explosive ammonium perchlorate.

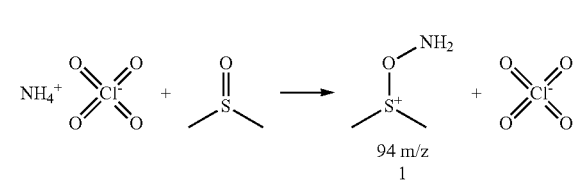

-continued

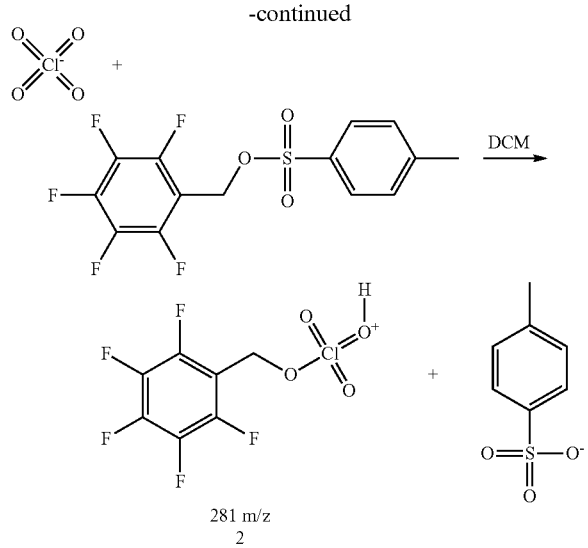

As shown in the reaction scheme, first volatile compound 1 and an isolated perchlorate anion are produced after the first organic reagent, DMSO, binds to the ammonium cation of the inorganic salt-based explosive. Second volatile compound 2 is produced after the second organic reagent, PFB-Tos, reacts with the isolated perchlorate anion of the inorganic salt-based explosive in the presence of dichloromethane solvent. In this particular embodiment, the toluenesulfonate group of the second organic reagent acts as a leaving group to facilitate the reaction between the second organic reagent and the isolated perchlorate anion. One or both of the first and second volatile compounds may be released from the carrier medium for subsequent processing. For example, after release, the first and second volatile compounds may be introduced into a chemical analyzer, such as a mass spectrometer, wherein the first and second volatile compounds may be analyzed such that the cation and the anion of the inorganic salt-based explosive may be detected indicating the presence of the salt on the carrier medium.

The first and second organic reagents may be applied to the sample individually or collectively. In some embodiments, the sample is treated with the first organic reagent prior to being treated with the second organic reagent. In some embodiments, the sample is treated with the second organic reagent at the same time as being treated with the first organic reagent. The sample on the carrier medium may be treated with the first and second organic reagents in any manner sufficient to contact the reagents with the sample. For example, in some embodiments, the first and second organic reagents may be sprayed or dripped onto the carrier medium. In some embodiments, the carrier medium, such as a pad, wipe, swab, or any other object that may be used to collect a sample, may be preimpregnated with the first and second organic reagents such that when the carrier medium contacts a sample, the sample will be treated with the first and second organic reagents.

In accordance with the methods of the present disclosure, when the first and second volatile compounds are produced, releasing the treated sample from a carrier medium should release at least one of the first and second volatile compounds from the carrier medium. In some embodiments, releasing the treated sample from a carrier medium releases both of the first and second volatile compounds from the carrier medium.

The treated sample may be released from the carrier medium by at least one technique chosen from reducing pressure on the treated sample and heating the treated sample. Reducing pressure on the treated sample and/or heating the treated sample may be used to affect the release of the treated sample from a carrier medium through vaporization.

To reduce the pressure on the treated sample, the treated sample should be located in a sealed environment. The sealed environment, such as a sealed sample chamber, may be coupled to a vacuum pump such that the vacuum pump can reduce the pressure on the treated sample to a pressure below atmospheric pressure.

The methods according to the present disclosure are not restricted to any particular method of heating the treated sample. For example, the treated sample may be heated directly or indirectly. In some implementations, the treated sample is heated by heating the carrier medium. The carrier medium may be heated, for example, using an infrared heating element positioned to emit radiant energy toward the carrier medium. The carrier medium may be heated by radiant energy of other wavelength ranges including UV, as well as wavelengths specifically chosen for a particular sample. Other techniques or materials may also be used to affect the release or vaporization of the sample from the carrier medium, including, for example, inductive heating or the use of a conductive heating element heated by Joule heating. Alternatively, an electrical current may be passed through an electrically conductive carrier medium, such as a carbon cloth, in order to heat the carrier medium and release the treated sample.

The present disclosure permits great flexibility in how the treated samples may be released from the carrier medium. As one of ordinary skill in the art will appreciate, the temperature at which a chemical is converted to a gas is a function of pressure. As an internal pressure in the sample chamber is reduced, the temperatures at which the treated sample will vaporize is reduced. Thus, treated samples may be released by reducing pressure on the treated sample, heating the treated sample, a combination thereof. For example, in some embodiments, the first and second volatile compounds may be released from the carrier medium by heating the compounds. If the internal pressure of the sample chamber is reduced to a pressure equal to or less than the vapor pressures of the first and second volatile compounds, the first and second volatile compounds may be released without the addition of heat. If the internal pressure of the sample chamber is reduced to a pressure below atmospheric pressure but greater than the vapor pressures of the first and second volatile compounds, the treated sample can be heated to vaporize the first and second volatile compounds at reduced boiling points. Thus, while the treated sample may be released by reducing pressure or heating, releasing the treated sample may also be controlled by a combination of reduced pressure and heat. Further, because the identity of the first and second organic reagents are known, the boiling points/vapor pressures of the first and second volatile compounds may be predicted or estimated for purposes of designing appropriate pressure and/or temperature release parameters. First and second organic reagents may also be chosen as described herein and by considering desired boiling points/vapor pressures of the first and second volatile compounds.

In accordance with the present disclosure, prior to treating the sample with the first and second organic reagents, the sample chamber housing the sample on a carrier medium may be evacuated using a vacuum pump or roughing pump to reduce an internal pressure of the sample chamber to a level below atmospheric pressure. Upon formation of the first and second volatile compounds, one or both of the first and second volatile compounds will be released from the carrier medium the pressure in the sample chamber was reduced to a pressure equal to or less than one or both of the vapor pressures of the first and second volatile compounds. If the pressure in the sample chamber was reduced to a pressure greater than one or both of the vapor pressures of the first and second volatile compounds, one or both of the compounds may be released by further reducing the internal pressure in the sample chamber and/or heating the treated sample.

In some implementations, the heating and/or reduction of pressure on the treated sample may be controlled such that components of the treated sample having different boiling points/vapor pressures are released from a carrier medium at different times. For example, in some embodiments, the heating and/or reduction of pressure on the treated sample may be controlled to allow the first and second volatile compounds to be released from a carrier medium at different times.

In some implementations of the present disclosure, the method of releasing a sample from a carrier medium may further comprise introducing a released sample into a chemical analyzer. In some embodiments, the step of releasing the treated sample from a carrier medium includes introducing the treated sample into a chemical analyzer. The chemical analyzer may be any equipment configured to receive and analyze a released sample. For example, the chemical analyzer may be a mass spectrometer, a gas chromatograph or a combination thereof.

A sample on a carrier medium may be treated with the first and second organic reagents in any environment sufficient to contact the first and second organic reagents with the sample. In one aspect of the present disclosure, a sample on a carrier medium is treated with the first and second organic reagents inside of a sample chamber, such as sample chamber 110 shown in FIG. 1. FIG. 1 illustrates an exemplary chemical detection system 100 with a sample chamber 110 configured to facilitate the release of a sample from a carrier medium. Sample chamber 110 has a base 112 and a lid 114. Base 112 and lid 114 define a cavity 111 configured to receive a sample on a carrier medium 125. In some embodiments, the base 112 and lid 114 define a substantially air-tight cavity 111. When base 112 and lid 114 define a substantially air-tight cavity 111, sample chamber 110 may comprise, for example, one or more gaskets or seals 113. In some implementations, base 112 and lid 114 are mechanically coupled, for example, by hinge 116 or other similar mechanisms, such that base 112 and lid 114 can be separated to allow access to cavity 111 for insertion and removal of carrier medium 125.

Sample chamber 110 has spraying system 120 configured to spray at least one reagent on carrier medium 125. As shown in FIG. 1, spraying system 120 may comprise a spray pump 160 and a spray nozzle 115 configured to spray at least one reagent on carrier medium 125. Although not shown in FIG. 1, spraying system 120 may comprise more than one spray pump and/or more than one spray nozzle. In some implementations, spraying system 120 is configured to spray the first and second organic reagents on carrier medium 125 as described herein. As shown in FIG. 1, spraying system 120 may be configured to spray the first and second organic reagents collectively out of spray nozzle 115 onto carrier medium 125 upon opening valve 135. Alternatively, spraying system 120 may utilize a valve system that allows the first and second organic reagents to be sprayed individually out of spray nozzle 115. In other implementations, the first and second organic reagents may be sprayed out of separate spray nozzles onto carrier medium 125.

Sample chamber 110 may optionally be coupled to a chemical analyzer 150 via, for example, path 130, valve 132, and port 117 defined by lid 114. In general, port 117 is located adjacent to cavity 111 to facilitate the introduction of a released sample into chemical analyzer 150. Valve 132 is operable to isolate an inlet port or analysis chamber of chemical analyzer 150 from sample chamber 110.

As shown in FIG. 1, sample chamber 110 may optionally be coupled to vacuum pump 140 via path 130, valve 133, and port 117. In general, port 117 is located adjacent to cavity 111 to facilitate the evacuation of the dead volume within cavity 111 and to reduce an internal pressure of sample chamber 110 to a level less than atmospheric pressure using vacuum pump 140. In implementations using vacuum pump 140, valve 134, as shown in FIG. 1, is operable to re-pressurize sample chamber 110 after operation of chemical detection system 100 to allow an operator to open the sample chamber, extract the carrier medium, and insert the next sample carried on a carrier medium.

A sample on a carrier medium inside of a sample chamber, such as sample chamber 110, may be released from the carrier medium as described in the process flow diagram of FIG. 2. In accordance with FIG. 2 and as described herein, in operation, spraying system 120 is used to spray the first organic reagent on carrier medium 125 and to spray the second organic reagent on carrier medium 125 to treat the sample with the first and second organic reagents. As described above, spraying system 120 may spray the first or second organic reagents individually or collectively onto carrier medium 125. Thus, in some embodiments, the second organic reagent is sprayed on carrier medium 125 after spraying the first organic reagent on the carrier medium. In other embodiments, the second organic reagent is sprayed on carrier medium 125 at the same time as spraying the first organic reagent on the carrier medium.

In accordance with the process flow diagram in FIG. 2, after treating the sample with the first and second organic reagents, the treated sample is released from carrier medium 125. The releasing step should be capable of releasing one or both of the first and second volatile compounds from carrier medium 125.

The treated sample may be released from carrier medium 125 using one or both techniques chosen from reducing pressure on the treated sample and heating the treated sample. In some implementations, heating the treated sample is accomplished by heating carrier medium 125 using infrared heating elements 160, as shown in FIG. 1. Infrared heating elements 160 are positioned so that they emit radiant energy substantially toward carrier medium 125 through a substrate 118 (e.g., fused quartz window) forming a portion of base 112. Heating carrier medium 125 may be accomplished via a variety of mechanisms, including, for example, controlling the temperature of a conductive heating element by adjusting voltage and current, and hence energy density (Joule heating), adjusting the frequency, wavelength, or intensity of a radiant source (e.g., infrared diodes), modulating the pulse width and/or frequency of a radiant source (PWM), and similar techniques. Other techniques for adjusting the temperature of carrier medium 125 can be realized without changing the scope of this disclosure.

The treated sample may also be released by reducing pressure on the treated sample on carrier medium 125, or by reducing pressure on the treated sample in combination with heating the treated sample. The pressure can be reduced using vacuum pump 140. With valves 134 and 132 closed and valve 133 open, vacuum pump 140 can reduce the pressure in substantially air-tight cavity 111 to a level less than atmospheric pressure. When used in combination with heating to affect the release of the treated sample, reducing the pressure on the treated sample can reduce the amount of heating energy required to release the treated sample from the carrier medium.

In some implementations, once the treated sample is released from carrier medium 125, the released sample may be introduced into chemical analyzer 150. The released sample can be introduced into chemical analyzer 150 via port 117 and path 130 with valves 133 and 134 closed and valve 132 opened. In some implementations, heating of the treated sample and/or reduction of pressure on the treated sample can be controlled and valve 132 operated such that analytes are released and introduced into chemical analyzer 150 at different times. In certain examples, the pressure of cavity 111 is adjusted in a pattern, with either substantially constant temperature or a corresponding temperature profile, to allow selective release of analytes, such as the first and second volatile compounds, from carrier medium 125. As described herein, the releasing step is capable of releasing one or both of the first and second volatile compounds from carrier medium 125. When both of the first and second volatile compounds are released from carrier medium 125 and introduced into chemical analyzer 150, the first and second volatile compounds may be detected, allowing for the detection of an inorganic salt-based explosive. In addition, the first organic reagent, as described herein, is also capable of dissolving organic compounds, such as most organic explosives. Thus, the methods according to the present disclosure allow for the release of organic explosive materials from carrier medium 125, enabling these materials to be detected in chemical analyzer 150.

In another implementation of the present disclosure, in accordance with the process flow diagram in FIG. 3, substantially air tight cavity 111 housing a sample on carrier medium 125 may be evacuated using vacuum pump 140 prior to treating the sample on carrier medium 125 with the first and second organic reagents. With valves 134 and 132 closed and valve 133 opened, vacuum pump 140 can evacuate cavity 111 in sample chamber 110 via port 117 and path 130. By evacuating the dead volume in sample chamber 110 prior to treating the sample with the first and second organic reagents and to the subsequent release of the treated sample, the effective concentration of the sample introduced into chemical analyzer 150 can be increased over that of a sample introduced from a non-evacuated chamber. This concept is described in U.S. Patent Publication No. 2012/0180576, which is incorporated by reference herein in its entirety. In addition, evacuating sample chamber 110 will reduce an internal pressure of sample chamber 110 to a level less than atmospheric pressure, which, in some implementations, can lead to the release of the sample from carrier medium 125 upon treatment, or can at least facilitate the release of the sample after treatment by reducing the boiling points of the first and second volatile compounds.

As shown in FIG. 3, after evacuating the sample chamber, the method proceeds as described herein, that is, the sample is treated with the first organic reagent and is treated with the second organic reagent, followed by release of the treated sample from the carrier medium. As described herein, the sample may be treated with the first and second organic reagents simultaneously or at different times. Also, as described herein, the released sample may be introduced into a chemical analyzer 150 for analysis.

Figure 4:
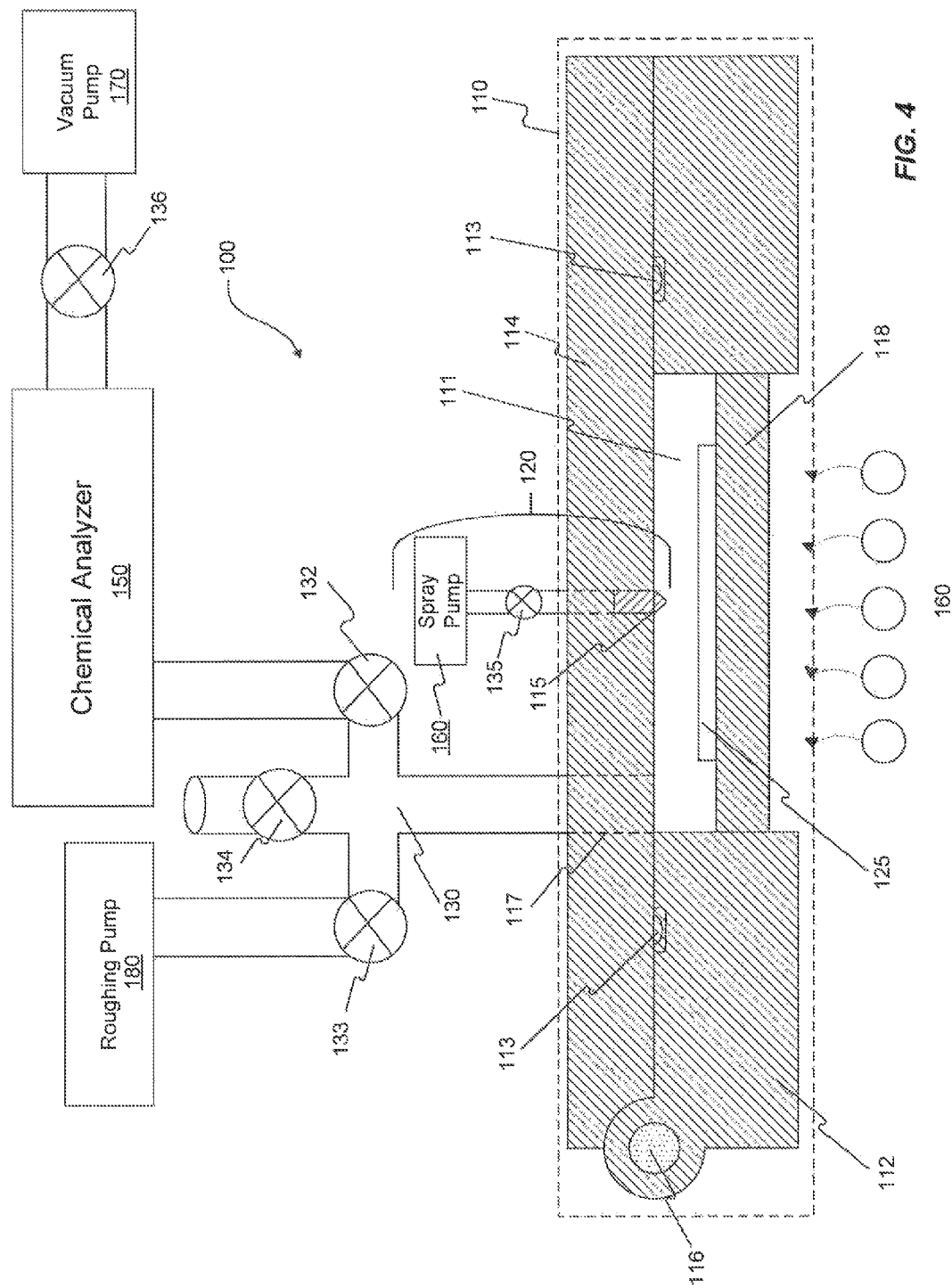
FIG. 4 is a schematic diagram of an exemplary chemical detection system, in accordance with some disclosed embodiments.

The arrangement shown as chemical detection system 100 in FIG. 1 is a non-limiting, exemplary arrangement. Other arrangements are possible, including, for example, using a vacuum pump coupled to sample chamber 110 via a vacuum path isolated from chemical analyzer 150, or using a vacuum pump system coupled to chemical analyzer 150, such as directly coupled to chemical analyzer 150. FIG. 4, for example, shows a chemical detection system where a vacuum pump 170 is directly coupled to chemical analyzer 150. Vacuum pump 170 can be used to at least partially evacuate sample chamber 110. In particular, vacuum pump 170 may be used to reduce the pressure in cavity 111. As described herein, reducing the pressure in cavity 111 and/or heating the treated sample may release the treated sample from carrier medium 125. The treated sample, namely the first and second volatile compounds, can be analyzed in chemical analyzer 150 as sample chamber 110 is evacuated by vacuum pump 170. As shown in FIG. 4, the detection system may optionally include a roughing pump 180. Roughing pump 180 can be used to at least partially evacuate air tight cavity 111 prior to treating the sample with the first and second organic reagents.

As should be apparent from the present disclosure, some embodiments may be carried out without the occurrence of a chemical process described herein. The occurrence of a chemical process described herein will depend upon the composition of the sample. Treating a sample on a carrier medium with the first and second organic reagents allows for an inorganic salt, such as an inorganic salt-based explosive, if present in the sample, to be transformed into volatile compounds capable of being released from the carrier medium for potential subjection to further processing, such as chemical analysis.

In the foregoing description of exemplary embodiments, various features are grouped together in a single embodiment for purposes of streamlining the disclosure. This method of disclosure is not to be interpreted as reflecting an intention that the claims require more features than are expressly recited in each claim. Rather, as the following claims reflect, inventive aspects lie in less than all features of a single foregoing disclosed embodiment. Thus, the following claims are hereby incorporated into this description of the exemplary embodiments, with each claim standing on its own as a separate embodiment of the invention.

Moreover, it will be apparent to those skilled in the art from consideration of the specification and practice of the present disclosure that various modifications and variations can be made to the disclosed systems and methods without departing from the scope of the disclosure, as claimed. Thus, it is intended that the specification and examples be considered as exemplary only, with a true scope of the present disclosure being indicated by the following claims and their equivalents.

What is claimed is:

1. A method comprising:
    treating a sample on a carrier medium with a first organic reagent;
    treating the sample on the carrier medium with a second organic reagent;
    releasing the treated sample from the carrier medium by vaporizing the treated sample; and
    analyzing the vaporized sample in a chemical analyzer.

2. The method of claim 1, wherein the first organic reagent comprises a polar aprotic solvent.

3. The method of claim 2, wherein the polar aprotic solvent is dimethyl sulfoxide (DMSO).

4. The method of claim 1, wherein the second organic reagent comprises a leaving group.

5. The method of claim 4, wherein the leaving group is sulfonate.

6. The method of claim 1, wherein the second organic reagent comprises a perfluorinated compound.

7. The method of claim 6, wherein the perfluorinated compound is a perfluoroalkyl or a perfluoroaryl.

8. The method of claim 6, wherein the perfluorinated compound is a perfluoroalkyl sulfonate or a perfluoroaryl sulfonate.

9. The method of claim 6, wherein the perfluorinated compound is pentafluorobenzyl-toluenesulfonate (PFB-Tos).

10. A method comprising:
    treating a sample on a carrier medium with a first organic reagent, wherein when the sample contains at least one inorganic salt, the first organic reagent binds to a cation of the inorganic salt to produce both a first volatile compound and an isolated anion of the inorganic salt;
    treating the sample on the carrier medium with a second organic reagent, wherein the second organic reagent reacts with the isolated anion to produce a second volatile compound;
    releasing the treated sample from the carrier medium by vaporizing the treated sample, wherein when the first and second volatile compounds are produced, the releasing step releases at least one of the first and second volatile compounds from the carrier medium; and
    analyzing the vaporized sample in a chemical analyzer.

11. The method of claim 10, wherein the releasing step releases both the first and the second volatile compounds from the carrier medium.

12. The method of claim 10, wherein the first organic reagent comprises a polar aprotic solvent.

13. The method of claim 12, wherein the polar aprotic solvent is dimethyl sulfoxide (DMSO).

14. The method of claim 10, wherein the second organic reagent comprises an organic reagent that is capable of undergoing a nucleophilic substitution reaction with the isolated anion.

15. The method of claim 14, wherein the organic reagent that is capable of undergoing a nucleophilic substitution reaction with the isolated anion comprises a sulfonate leaving group.

16. The method of claim 10, wherein the second organic reagent comprises a perfluorinated compound.

17. The method of claim 16, wherein the perfluorinated compound is a perfluoroalkyl or a perfluoroaryl.

18. The method of claim 16, wherein the perfluorinated compound is a perfluoroalkyl sulfonate or a perfluoroaryl sulfonate.

19. The method of claim 16, wherein the perfluorinated compound is pentafluorobenzyl-toluenesulfonate (PFB-Tos).

20. The method of claim 10, wherein the first organic reagent comprises a polar aprotic solvent, and the second organic reagent comprises an organic reagent capable of undergoing a nucleophilic substitution reaction with the isolated anion.

21. The method of claim 10, wherein the sample on a carrier medium is treated with the second organic reagent at the same time as being treated with the first organic reagent.

22. The method of claim 10, wherein the step of releasing the treated sample from the carrier medium comprises at least one technique chosen from reducing pressure on the treated sample and heating the treated sample.

23. The method of claim 22, wherein the step of releasing the treated sample from the carrier medium comprises heating the treated sample after reducing pressure on the treated sample.

24. The method of claim 22, wherein the step of releasing the treated sample occurs in a sample chamber, and reducing pressure on the treated sample comprises evacuating the sample chamber to reduce an internal pressure of the sample chamber to a pressure below atmospheric pressure.

25. The method of claim 24, wherein the released sample is introduced into a chemical analyzer during or after the evacuation of the sample chamber.

26. The method of claim 22, wherein the sample on a carrier medium is treated with the first and second organic reagents inside of a sample chamber, the method further comprising evacuating the sample chamber to reduce an internal pressure of the sample chamber to a pressure below atmospheric pressure prior to treating the sample with the first and second organic reagents.

27. The method of claim 10, wherein the sample on a carrier medium is treated with the first and second organic reagents inside of a sample chamber.

28. The method of claim 27, wherein the step of treating the sample on a carrier medium with a first organic reagent comprises spraying the first organic reagent on the carrier medium, and the step of treating the sample on a carrier medium with a second organic reagent comprises spraying the second organic reagent on the carrier medium.

29. The method of claim 28, wherein the first and second organic reagents are sprayed on the carrier medium at the same time.

30. The method of claim 27, wherein the method further comprises evacuating the sample chamber to reduce an internal pressure of the sample chamber to a level less than atmospheric pressure prior to treating the sample on the carrier medium with the first and second organic reagents.

31. The method of claim 10, wherein the carrier medium is pre-impregnated with one or both of the first and second organic reagents such that the sample is treated with one or both of the first and second organic reagents upon contact with the carrier medium.

32. The method of claim 1, wherein the chemical analyzer is a mass spectrometer.

33. The method of claim 1, wherein if the sample comprises an inorganic salt, the first organic reagent binds to a cation of the inorganic salt to produce both a first volatile compound and an isolated anion of the inorganic salt.

34. The method of claim 33, wherein if the isolated anion is produced, the second organic reagent reacts with the isolated anion to produce a second volatile compound.

35. The method of claim 34, wherein if the first and second volatile compounds are produced, the step of releasing the treated sample from the carrier medium comprises releasing one or both of the first and second volatile compounds from the carrier medium.

36. The method of claim 1, wherein the sample on a carrier medium is treated with the second organic reagent at the same time as being treated with the first organic reagent.

37. The method of claim 1, wherein the step of releasing the treated sample from the carrier medium comprises at least one technique chosen from reducing pressure on the treated sample and heating the treated sample.

38. The method of claim 1, wherein the sample on a carrier medium is treated with the first and second organic reagents inside of a sample chamber.

39. The method of claim 1, wherein the carrier medium is pre-impregnated with one or both of the first and second organic reagents such that the sample is treated with one or both of the first and second organic reagents upon contact with the carrier medium.

40. The method of claim 10, wherein the chemical analyzer is a mass spectrometer.

\* \* \* \* \*